United States Patent
Horstmann et al.

(10) Patent No.: US 10,596,126 B2
(45) Date of Patent: *Mar. 24, 2020

(54) TRANSDERMAL THERAPEUTIC SYSTEM COMPRISING ACTIVE INGREDIENT PARTICLES AND HAVING INCREASED ACTIVE INGREDIENT FLUX

(71) Applicant: LTS Lohmann Therapie-Systeme AG, Andernach (DE)

(72) Inventors: Michael Horstmann, Neuwied (DE); Mohammad Sameti, Bonn (DE); Tobias Jung, Mendig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,069

(22) Filed: Apr. 10, 2019

(65) Prior Publication Data

US 2019/0231710 A1    Aug. 1, 2019

Related U.S. Application Data

(63) Continuation of application No. 12/302,065, filed as application No. PCT/EP2007/004765 on May 30, 2007, now Pat. No. 10,292,942.

(30) Foreign Application Priority Data

Jun. 8, 2006   (DE) .................. 10 2006 026 578

(51) Int. Cl.
 *A61K 9/70*  (2006.01)

(52) U.S. Cl.
 CPC .......... *A61K 9/7069* (2013.01); *A61K 9/7092* (2013.01)

(58) Field of Classification Search
CPC combination set(s) only.
See application file for complete search history.

(56) References Cited

U.S. PATENT DOCUMENTS

| | | |
|---|---|---|
| 3,964,482 A | 6/1976 | Gerstel et al. |
| 4,460,372 A | 7/1984 | Campbell et al. |
| 4,687,481 A | 8/1987 | Nuwayser |
| 5,174,995 A | 12/1992 | Davis |
| 5,270,358 A | 12/1993 | Asmus |
| 5,716,636 A | 2/1998 | Horstmann et al. |
| 6,238,700 B1 | 5/2001 | Dohner et al. |
| 6,440,336 B1 | 8/2002 | Weinreich et al. |
| 10,292,942 B2 * | 5/2019 | Horstmann .......... A61K 9/7092 |
| 2004/0091542 A1 | 5/2004 | Watanabe et al. |

FOREIGN PATENT DOCUMENTS

| | | |
|---|---|---|
| CA | 2372710 A1 | 8/2000 |
| DE | 3910543 C2 | 10/1990 |
| DE | 19844079 A1 | 11/1999 |
| DE | 10136784 A1 | 2/2003 |
| EP | 0186019 A2 | 7/1986 |
| EP | 0364944 A1 | 4/1990 |
| EP | 0391172 C2 | 10/1990 |
| EP | 0481443 A1 | 4/1992 |
| EP | 0307187 B1 | 6/1995 |
| EP | 0739626 A2 | 10/1996 |
| IT | 2233688 A | 7/1986 |
| WO | 98/26762 A1 | 6/1998 |
| WO | 00/47191 A1 | 8/2000 |
| WO | 04/012721 A2 | 2/2004 |

OTHER PUBLICATIONS

M. J. Cappel et al., "Effect of nanoparticles on transdermal drug delivery", J. Microencapsulation (1991) vol. 8, No. 3, pp. 369-374.
M. Ricci et al., "Evaluation of Indomethacin Percutaneous Absorption from Nanostructured Lipid Carriers (NLC): In Vitro and In Vivo Studies", J. Pharmaceutical Sciences (2005) vol. 94, No. 5, 1149-1159.
"Physikalische Chemie" VEB deutscher Verlag fur Grundstoffindustrie, Leipzig (1974), 384-387.
Kummel et al. GIT labor-Fachzeitschrift (1999) pp. 511-514.
K. A. Walters et al., "Dermatological Formulation andTransdermal Systems", Brain in dermatological and Transdermal Formulations, NY (2002) Marcel Dekker, 319-399.

* cited by examiner

*Primary Examiner* — Hasan S Ahmed
(74) *Attorney, Agent, or Firm* — ProPat, LLC; Cathy R. Moore

(57) ABSTRACT

The present invention relates to a transdermal therapeutic system, preferably a transdermal patch, having an active ingredient-containing matrix formed substantially of a water-insoluble base material, such as rubber and synthetic polymers, into which is incorporated water-soluble and/or water-swellable inclusion bodies, e.g. inclusion bodies formed from polyvinyl alcohol or polyethylene glycol, that further include micronized or nanoscale active ingredient particles.

18 Claims, 2 Drawing Sheets

TRANSDERMAL THERAPEUTIC SYSTEM COMPRISING ACTIVE INGREDIENT PARTICLES AND HAVING INCREASED ACTIVE INGREDIENT FLUX

CROSS-REFERENCE TO RELATED APPLICATIONS

This application is a Continuation Application of U.S. patent application Ser. No. 12/302,065, filed. Nov. 24, 2008, allowed, which was a National Stage Application of International Application No. PCT/EP2007/004765, filed May 30, 2007, which claimed priority to German Patent Application No. 10 2006 026 578.5, filed Jun. 8, 2006. Each of U.S. patent application Ser. No. 12/302,065; International Application No. PCT/EP2007/004765 and German Patent Application No. 10 2006 026 578.5, are hereby incorporated herein by reference in their entireties.

FIELD OF THE INVENTION

The invention relates to transdermal therapeutic systems with included particulate active ingredient (inclusion bodies) which can be activated by moisture, for example moisture on the skin, and processes for producing such systems.

BACKGROUND OF THE INVENTION

Transdermal therapeutic systems (TTS) have been known for a number of years among those skilled in the art and have been launched on the market. Transdermal therapeutic systems are self-adhesive pharmaceutical preparations which are to be applied to the skin, have a fixed application area, and deliver a medicinal substance to the human or animal body in a manner controlled according to time and quantity.

The therapeutic advance of these systems by comparison with traditional administration forms is that the active ingredient is supplied to the body not intermittently, as for example on intake of tablets, but continuously.

This results on the one hand in extending the duration of action of a medicinal substance, and on the other hand substantially preventing side effects through avoiding unnecessary peaks in the blood level.

The forms normally employed for such systems are layered, flat and use various polymers, of which polyethylene terephthalate, polyisobutylene, polysiloxane are mentioned by way of example.

For the purpose of improving the adhesion to moist surfaces it is possible to introduce, besides numerous substances known to the skilled person (resins, oils, fillers, stabilizers), also water-soluble/swellable additions (EP 0307187). Nanoparticulate excipients have also been employed experimentally as excipients for transdermal delivery (J. Microencaps. (1991), p. 369-374), although with limited success. Besides the more customary polymeric excipients, experiments have also been carried out with nanostructured lipid carriers for active ingredients, e.g. with indomethacin (J. Pharm. Sei. (2005), p. 1149-1159).

The opinion prevailing among experts in the early days of transdermal systems was that the main difficulty of delivery through the skin was the need to control the rate of delivery. For this reason, membranes controlling the active ingredient and, inter alia, also the optional absorption enhancer were introduced into such systems (here for example U.S. Pat. No. 4,460,372). Attempts were also made to regulate the control of delivery in this way by particle sizes of varying dimensions extending to micro- and nanoparticles (U.S. Pat. No. 4,687,481).

Since the human skin does not, however, have a permeability sufficient for all medicinal substances under consideration, only a small number of active ingredients can be employed in transdermal therapeutic systems of the conventional type. Numerous attempts have therefore been made with the aim of increasing the natural permeability of skin.

One such possibility is to use so-called penetration enhancers or absorption promoters. By these are meant substances which achieve a marked increase in the active ingredient flux by chemical/physical interaction with the microstructure of the skin. However, many of these substances have a toxic effect on the skin or cause irritation. Nor is the onset of the effect of these absorption promoters always sufficiently fast, so that the effect is difficult to control.

Another possibility is the use of physical principles such as, for example, of ionophoresis, of ultrasound-assisted permeation enhancement (sonophoresis) or else the use of microneedles (e.g. U.S. Pat. No. 3,964,482). However, these methods require comparatively elaborate additional devices in the transdermal therapeutic system, which ordinarily make this type of therapy uneconomical.

A fundamentally different way of increasing the permeability of skin is to increase the thermodynamic activity of the active ingredient. Attempts to this aim at increasing the active ingredient concentration acting from the outside in order to increase the permeation. These efforts were limited by the fact that it is not generally possible to increase the concentration of an active ingredient above the saturation solubility. On the other hand, the use of formulation bases with greater solubility for the active ingredient in the transdermal therapeutic system is no help because, in such cases, the link between the partition coefficient and solubility according to Nernst's partition law comes into operation and has a limiting effect.

It is possible for so-called supersaturated states to arise temporarily, where the dissolved active ingredient concentration is above the saturation concentration, e.g. when a saturated solution is cooled. Such systems are described for example in U.S. Pat. No. 5,174,995, in which saturated solutions of active ingredients are placed on the skin and lead, through the influence of the de-solubilizing effect of the moisture on the skin, to supersaturation and thus increased transport of active ingredient. It is obvious that utilization of such states in liquids rapidly fails through precipitation of the active substance and accordingly reduced concentrations and delivery rates. Supersaturated states can be generated and maintained longer in transdermally customary adhesive polymers than in solutions of liquid media (J. Pharm. Sci. (2004), p. 2039-2048). A concentration of up to four times the saturation solubility was successfully maintained for minutes to days here. However, even this stability is far from sufficient for marketable transdermal systems. With certain active ingredients whose melting point is not much above room temperature, such as, for example, scopolamine, such supersaturations can, however, be stabilized in some circumstances for a sufficiently long time through technical production measures (U.S. Pat. No. 6,238,700).

A stable system cannot be achieved with this proposed solution for active ingredients which are in particulate form and whose melting point is distinctly above room temperature (thus above about 50° C.). It is, however, possible to achieve a storable system by combining a layer which limits the access of moisture from the skin, and a matrix with water-insoluble base material and, present therein, inclusions which in turn comprise the active ingredient as disclosed in DE 39 10 543, which system enters a supersaturated state only on exposure to moisture from the skin and thus brings about the desired increased active ingredient flux only on use, Unfortunately, the solution to the problem according to the present state of the art is still associated with disadvantages. Thus, the solution proposed in DE 39 10 543 requires the active ingredient to be incorporated in dissolved (solid-dissolved) form. This is associated with the risk of premature inactivation of sensitive active ingredients through chemical degradation, since active ingredients are less stable in solution than in solid crystalline form (U.S. Pat. No. 5,716,636), It is moreover difficult to adjust the extent and the time course of the supersaturation, because they depend greatly on the degree of swelling of the inclusions (islands) in connection with the obligatory layer which limits the access of moisture. A further disadvantage of this prior art is, again because of the requirement to provide a dissolved inner phase of the active ingredient, the need to employ a comparatively large amount of excipient for the base material of the islands, because otherwise slightly soluble medicinal substances cannot be converted into a solid solution. This makes it difficult or impossible to design flexible and thin patches which are preferred by consumers and patients.

SUMMARY OF ADVANTAGEOUS EMBODIMENTS OF THE INVENTION

It is therefore an object of the invention which is described in detail below to provide transdermal therapeutic systems with increased active ingredient flux and, compared with the prior art, improved stability, improved uniformity in the provision of the increased active ingredient flux and less use of excipients.

DETAILED DESCRIPTION OF ADVANTAGEOUS EMBODIMENTS OF THE INVENTION

Figure 1:
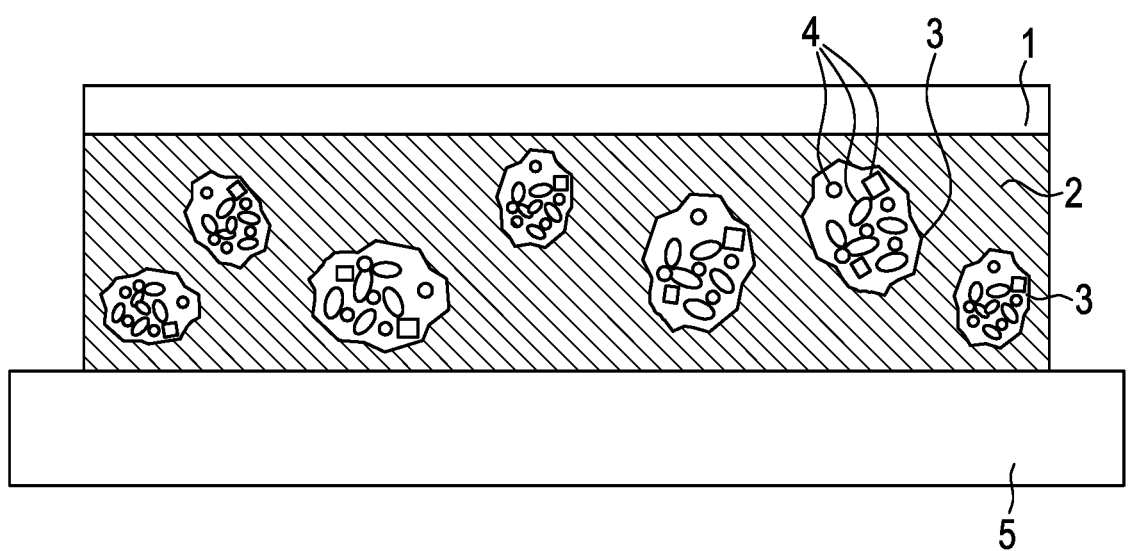
FIG. 1 is a cross-sectional illustration of an exemplary transdermal therapeutic system in accordance with the invention including a backing layer, an active layer and a protective film.

This object is achieved according to the invention by a transdermal therapeutic system which preferably has a backing layer which limits the diffusion of water and faces outwards, and has, located within a coherent, essentially water-insoluble outer phase (base material), numerous inclusion bodies (islands) which are separated from one another and which consist of a water-soluble or water-swellable material and comprise the major part of the active ingredient content of the formulation, the major part of which content in turn is present in a particulate, microparticulate or nanoparticulate state.

Essential constituents of the base material which are to be mentioned by way of example are polymers such as rubber, rubber-like synthetic homopolymers, copolymers or block polymers, polyacrylic acid esters and copolymers thereof, polyurethanes, ethylene copolymers, polyisobutylene, polybutylene and polysiloxanes. All polymers which are essentially insoluble in water and exert no disadvantageous effects on humans in direct and indirect contact with the skin are suitable in principle.

Since the adhesive bond can also be effected by an additionally applied adhesive layer, the base material need not necessarily be formulated to be primarily adhesive, but this property is preferred for a particularly thin and flexible, non-applying system structure which would also make a monolayer system possible. Further substances known to the skilled person and having a functional influence on the base material can be employed, such as, for example, plasticizers, tackifiers, absorption promoters, stabilizers or fillers.

Suitable excipients which can be employed in the first place for building up the active ingredient-containing inclusion bodies are water-soluble or water-swellable polymers. Examples of these which should be mentioned are: polyvinyl alcohol and its copolymers, polyvinylpyrrolidone and its copolymers, polyethylene glycols, preferably with a molecular weight of more than 1000 daltons (and which are thus solid at room temperature). The above polymers may themselves consist of particulate crosslinked structures, as is advantageous for controlled dispersion of the inclusion bodies in the base material. Further polymers which can be employed satisfactorily are alginates, pullulan, guar gum with gum arabic or other vegetable gums, cellulose, especially microcrystalline cellulose and its derivatives such as, for example, methylcellulose, hydroxyethylcellulose, hydroxymethylpropylcellulose etc., but also other carbohydrates such as, for example, starch, particularly preferably in derivatized or modified form. However, peptide polymers such as collagen and gelatin are also perfectly suitable. Water-soluble and water-swellable polymers have the advantage that they become more ductile and more diffusible only gradually, not suddenly on uptake of water, and thus deliver the included active ingredient(s) more uniformly. This is worthwhile especially in applications where the dispersed active ingredient particles are to be included in the active ingredient delivery process only stepwise.

If a more rapid transition is preferred, water-soluble substances with smaller molecules are advantageously to be employed as sole or admixed excipients for building up the active ingredient-containing inclusion bodies. Primarily suitable for this purpose, because of their property of forming diffusion-resistant particles which form a glass-like solid, are sugars and their derivatives, predominantly sucrose, glucose, lactose, fructose, but also sugar alcohols such as sorbitol or mannitol. Also suitable in principle are all pharmaceutically compatible water-soluble substances which have the property of liquefying under a water vapor tension of about 98 percent relative humidity (as provided by the skin), such as, for example, sodium chloride, urea, malic acid, citric acid.

Additions to achieve further functionalities known to a skilled person, such as, for example, stabilizers (especially antioxidants), fillers, but also modifiers having a micellar action (lecithins) can be provided according to the particular requirement.

Since it is essential for the inventive purpose that the inclusion bodies form as isolated internal phase in the base material/outer phase, it is possible to add as phase formers corpuscular hydrophilic particles, such as finely dispersed silica gel, nanodisperse silicon dioxide, calcium sulfate, but also polymers such as cellulose derivatives and other substances already mentioned for example hereinbefore as possible polymers for inclusion bodies.

Besides the complex which is essential to the invention and is composed of base material and inclusion body, which in the simplest case can form together merely with a backing layer a complete TTS system, it is possible and worthwhile to combine further system constituents known to those skilled in the art with the inventive principle.

The TTS of the invention, probably in the form of a transdermal patch, can thus in principle have a structure like systems known in the prior art. The difference which is essential to the invention comprises the active ingredient reservoir (active ingredient matrix) which is improved according to the invention and which is composed of essentially water-insoluble base material which has water-soluble or water-swellable inclusion bodies which comprise the active ingredient particles (particulate phase).

Of the abovementioned further system constituents, mention should be made for example of polymer-containing layers or else membranes which may have a property controlling the active ingredient flux to the skin, or else are able to moderate excessively fast uptake of moisture from the skin.

Materials customarily known to the skilled person for such membranes are polyethylene, polyamide, ethylene-vinyl acetate copolymers, but also porous layers filled with low molecular weight substances, Without or with use of a membrane it is also possible to apply additional adhesive layers to improve the fixing on the skin, of which the essential excipients have already been mentioned hereinbefore in the explanation of the base materials. Mention should be made here particularly preferably of highly diffusible lipophilic polymers such as, for example, polysiloxanes and acrylate copolymers. The principle of the invention can additionally be combined with further methods for absorption enhancement. Thus, it is possible to add penetration enhancers which increase the permeability of the skin and to employ physical principles such as iontophoresis, electroporation or else ultrasound and microneedles.

Suitable active ingredients employed for the active ingredient particles are preferably substances whose melting point is above 50° C. Mention should be made here by way of example of atropine, chlorpromazine, haloperidol, ephedrine, propanolol, clonidine, moxonidine, fentanyl, indomethacin, ethinylestradiol, desogestrel, testosterone, granisetron, pramipexole, tetrahydrocannabinol, vinpocetine besides many other substances. However, active ingredients which are liquid at room temperature are also suitable as long as they can be converted into a colloidal form. This group includes for example nicotine, nitroglycerin, selegiline, bupropion.

This list is not exhaustive because in principle all active ingredients which are suitable pharmaceutically for transdermal administration and belong to numerous indication groups can be employed. Particularly preferred active ingredients are those whose saturation flux on the skin is insufficient without the use of further principles for absorption enhancement. To find these particularly suitable active ingredients, a skilled person will carry out preliminary tests with permeation investigations on isolated pieces of skin by determining the delivery rate per square centimeter to be found at saturation in an inert medium. It is therefore possible to select as particularly preferred candidates those active ingredients whose saturation flux (i.e. the delivery rate without use of the principle of the invention), calculated for a commercially relevant system area of 30 cm$^2$, is 50% or less of the therapeutically necessary dose.

The particle size of the active ingredient particles is in principle unrestricted as long as it is distinctly (preferably less than 20%, particularly preferably less than 10% and very particularly preferably less than 5%) below the particle size of the inclusion bodies (this is typically less than or equal to 50 µm, preferably 10-50 µm). The full inventive advantage is achieved with a particularly small particle size of the active ingredient through the possibility of utilizing an increase in the saturation solubility and thus in the thermodynamic activity.

Particular advantages of the present invention also derive from the stabilization of very finely divided active ingredient particles. It should he mentioned in this connection that the well-known phenomenon of "Ostwald ripening" otherwise results in a physical destabilization:

finely dispersed micronized or even nanoscale particles are prone to coarsening of the particle, resulting in a reduced surface energy. This phenomenon is observed especially when the active ingredient particles are connected together by a diffusive medium and then large particles can grow at the expense of smaller ones, which then dissolve.

The provision according to the invention of an excipient complex of the inclusion bodies which has become difficultly diffusible through drying or water or solvent removal results in the transdermal therapeutic systems remaining substantially protected from the effect of Ostwald ripening/recrystallization during storage. It is thus possible to store stably even particles which have a diameter distinctly below 1-10 µum, preferably even below 50 nm. As soon as this system is applied to the skin, the increased, thermodynamically related saturation solubility of the particles has a positive effect in relation to increasing the active ingredient flux. The observation of the increased saturation solubility (not only dissolution rate) of such small particles is also derived from Ostwald and is described by the formula of the "Ostwald-Freundlich law" ("Physikalische Chemie", VEB deutscher Verlag für Grundstoffindustrie, Leipzig 1974, page 384).

Methods for generating such small particle sizes of active ingredient crystals are known to the skilled person and are not critical for the functionality of the invention. Possible ways of controlled precipitation can be categorized as basic pharmaceutical operations that result for example from mixing a saturated active ingredient solution in a solvent to which a poorer solvent is added stepwise with continuous mixing.

The resulting particles can be generated at virtually any stage, even at the colloid stage, ideally even on addition of the substances or substance mixtures serving later as inclusion bodies, through removal of the solvent (drying, spray drying, surface drying). Other possible ways of generating nanoscale or microscale active ingredients result from techniques of bead mill grinding or homogenization of particles in aqueous or nonaqueous environment.

Reference may be made by way of example for a brief compilation to Bushrab and Müller (New Drugs, edition 5, 2003), but also other processes such as that of generation by supercritical carbon dioxide (Kümmel et al, GIT Labor-Fachzeitschrift 5/99, (1999) pages 511-514), can also be used.

The backing layer of transdermal systems for the purpose of the invention may consist for example of a polyester (polyethylene terephthalate) membrane which has a water vapor-barrier-occlusive effect and which protects both from loss of active ingredient and from loss of moisture, Appropriate adaptation of the thickness or choice of other materials (polyethylene, polyurethane, or laminates of various thermoplastic raw materials) makes it possible to moderate the loss of water vapor and thus to accurately adjust the resulting state of swelling or dissolution of the inclusion bodies.

The systems of the invention themselves can be produced in diverse ways. The following possibilities are particularly emphasized and preferred, but ultimately as examples, and relate in particular to the production of the active ingredient reservoir (base material with active ingredient-containing inclusion bodies) of the invention.

Otherwise, the construction/production of the TTS of the invention (layer structure, materials, excipients and additives) can take place as described by the methods known to the skilled person from the prior art (see, for example, "Dermatological Formulation and Transdermal Systems", Kenneth A. Walters and Keith R. Brain in Dermatological and Transdermal Formulations, NY 2002, Marcel Dekker, pages 319-399):

1. Dispersing the micronized or nanoscale active ingredient particles in an aqueous solution of the excipient(s) for building up the active ingredient-containing inclusion bodies, which avoids dissolution of the active ingredient particles, and subsequent drying. The drying can take place for example by spray drying, in which case finely divided particles are obtained immediately, or else by surface drying with subsequent comminution of the particles. The inclusion bodies obtained in this way are fed into a solution or suspension of the base material which is present in organic solution or even solvent-free (hot-melt rapid process), whereupon after subsequent coating onto the backing layer and drying of the layer, a product already capable of functioning is obtained by cutting out. The active ingredient reservoir (base material and inclusion bodies) is in this case designed to be self adhesive.
2. Formulation of the solid inclusion bodies together with the active ingredient can also be achieved with the base material already present. To this end, a water-immiscible organic solution of the base material is generated by stirring, and in this a solution or dispersion of the excipients for building up the inclusion bodies (including active ingredient) in an aqueous mixture, or at least one consisting of polar solvent, is generated and is dispersed in the solution of the base material. The liquid/liquid dispersion is then likewise coated onto the backing layer sheet in a uniform layer thickness. The subsequent drying process leads to solidification of the inclusion bodies with loss of solvent. Suitable control of the drying process results, in the last stage of the removal of solvent, in the formation of nano- or microscale precipitated forms of the active ingredient in the inclusion bodies, whose further particle growth is suppressed by termination of the drying process.

One variant of this second process is to add already nanoscale active ingredients to the complete solvent mixture. A preferred enrichment of the active ingredient crystals in the preformulated inclusion bodies which still contain solvent as a rule takes place due to the wettability, which is improved as a result of the polarity, in the inner phase.

The exact choice of the dimensions of layer thicknesses and polarities of the individual system components must of course be established separately for each individual application. Two methods for controlling the extent of the active ingredient flux which has been increased according to the invention should be observed for the occurrence of the advantage of the invention:

1. The choice of the particle size of the particulate active ingredient content of the inclusion bodies, which results, according to the "Ostwald-Freundlich law" already mentioned, in a corresponding higher saturation solubility, and
2. the additional effect arising from the drying, taking place through heat, of the layers of the transdermal system, and may result in a supersaturation caused by the heat.

EXAMPLE 1

Production of Microparticles:

2.5 g of gelatin are dissolved in 100 ml of water at 50° C. Then 0.5 g of active ingredient crystals (testosterone, micronized) is suspended (4-blade stirrer, 500-1000 rpm) in the gelatin solution. The suspension is then tipped into a glass beaker which contains an aqueous solution of gum arabic (2.5%, w/v), 400 ml of water are added, the pH is reduced to 3.0-4.3 with hydrochloric acid (1 N), and the mixture is cooled to 4° C. After the microcapsules have deposited for two hours, the supernatant is decanted off and the particles are hardened by adding 2×150 ml of ethanol to the sediment. Finally, the microcapsules are filtered off and dried to constant mass overnight.

The produced particles are suspended in 10.0 g of silicone adhesive (e.g. Bio PSA 4201) and homogeneously stirred to give a composition. This composition is then spread with a manual knife coater on a flour polymerized 100 µm PET film in a layer thickness of 50 to 100 µm and dried at 30° C. and laminated with a transparent 15 µm PET film.

EXAMPLE 2

0.5 g of testosterone is dissolved in 10.0 g of a solution of ethylcellulose in ethanol (27.3% strength). The solution is then suspended in 14.0 g of silicone adhesive (e.g. Bio PSA 4201) and homogeneously stirred to give a composition. This composition is then spread with a manual knife coater on a flour polymerized 100 µm PET film in a layer thickness of 50 to 100 µm and dried at 80° C. and laminated with a transparent 15 µm PET film.

Figure 2:
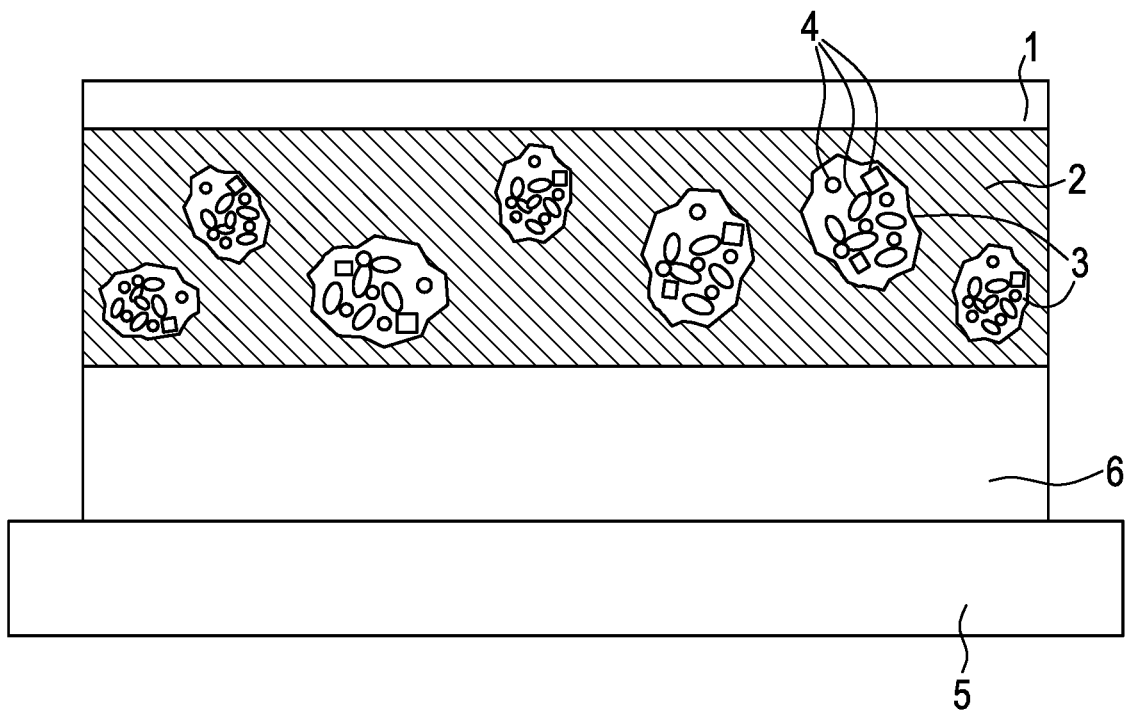
FIG. 2 is a cross-sectional illustration of an exemplary transdermal therapeutic system in accordance with the invention that further includes an additional adhesive layer.
Figure 3:
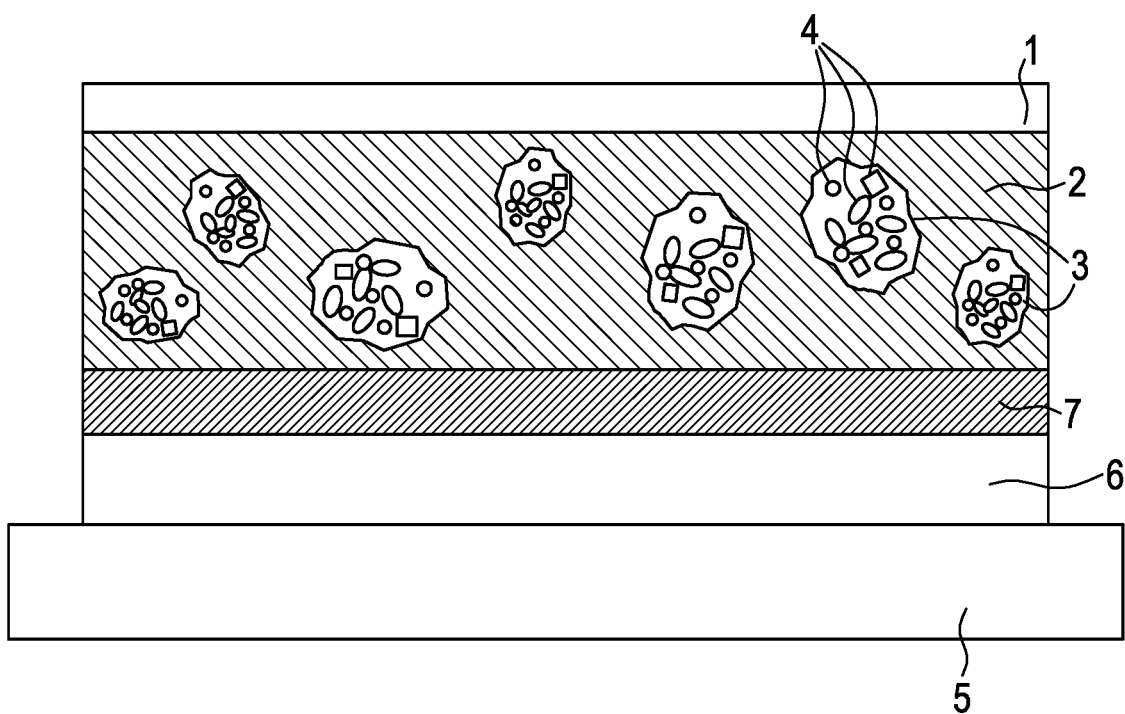
FIG. 3 is a cross-sectional illustration of an exemplary transdermal therapeutic system in accordance with the invention that further includes a control membrane.

The present invention is further explained in more detail by way of example by FIGS. 1 to 3;

FIG. 1 shows a TTS (transdermal patch) of the invention which consists of only two layers. The meanings are: (1) backing layer facing outward, (2) base material of the active layer—containing the active ingredient, (3) inclusion bodies which comprise the active ingredient particles (4), and (5) a detachable protective film which protects the TTS before use. After removal of the protective film (5), the TTS is applied with this self-adhesive side to the skin.

FIG. 2 shows a TTS of the invention which has an additional adhesive layer (6).

FIG. 3 shows a TTS of the invention which additionally has a control membrane (7).

That which is claimed:

1. A transdermal therapeutic system with an active ingredient-containing matrix comprising an essentially water-insoluble base material having inclusion bodies which are separated from one another, said inclusion bodies formed from a mixture of peptide polymer and vegetable gum containing active ingredient particles dispersed inside or suspended inside said mixture, wherein said active ingredient particles are micro- or nanoparticles, said active ingredient, in the state prior to the application of the transdermal therapeutic system to the skin, is neither liquid nor dispersed or suspended in liquid.

2. The transdermal therapeutic system as claimed in claim 1, wherein said peptide polymer is gelatin or collagen and said vegetable gum is gum arabic or guar gum.

3. The transdermal therapeutic system as claimed in claim 2, wherein said peptide polymer is gelatin, the vegetable gum is gum arabic and said mixture has been hardened.

4. The transdermal therapeutic system as claimed in claim 1, wherein said transdermal therapeutic system has a layered structure that includes two layers, said layers comprising a backing layer facing outward, and a layer comprising the active ingredient-containing matrix.

5. The transdermal therapeutic system as claimed in claim 1, wherein said transdermal therapeutic system comprises an adhesive layer.

6. The transdermal therapeutic system as claimed in claim 1, wherein said transdermal therapeutic system comprises a control membrane.

7. The transdermal therapeutic system as claimed in claim 1, wherein the inclusion bodies have a particle size of less than 50 μm.

8. The transdermal therapeutic system as claimed in claim 1, wherein the base material of the active ingredient matrix comprises rubber; rubber-like synthetic homopolymers, copolymers or block polymers; polyacrylic acid esters or copolymers thereof; polyurethanes; polyisobutylene; polybutylene or silicone adhesive.

9. The transdermal therapeutic system as claimed in claim 1, wherein the active ingredient is atropine, chlorpromazine, haloperidol, ephedrine, propranolol, clonidine, moxonidine, fentanyl, indomethacin, ethinylestradiol, desogestrel, testosterone, granisetron, pramipexole, tetrahydrocannabinol or vinpocetine.

10. A process for producing the active ingredient-containing matrix of a transdermal therapeutic system as claimed in claim 3, comprising the steps:
suspending the micronized or nanoscale active ingredient particles in a gelatin solution,
admixing the gelatin solution containing active ingredient particles into a gum arabic solution,
reducing the pH of the admixture to 3.0 to 4.3 and cooling the pH adjusted admixture to 4° C.,
depositing microcapsules comprising gelatin, gum arabic and active ingredient as sediment;
decanting the admixture,
hardening the sediment;
filtering the sediment and drying.

11. A process as claimed in claim 10, wherein the hardening step comprises adding ethanol.

12. A transdermal therapeutic system with an active ingredient-containing matrix, said matrix consisting of water-insoluble base material having inclusion bodies separated from one another, said inclusion bodies consisting of water-soluble or water-swellable material and active ingredient particles inside said water-soluble or water-swellable material,
wherein said active ingredient particles are micro- or nanoparticles and said active ingredient, in the state prior to the application of the transdermal therapeutic system to the skin, is neither liquid nor dispersed or suspended in liquid, said inclusion bodies optionally comprising either a sugar, sugar derivative or pharmaceutically compatible water-soluble substance that liquefies under a water vapor tension of about 98 percent relative humidity.

13. The transdermal therapeutic system as claimed in claim 12, wherein (i) said sugar or sugar derivative is selected from sucrose, glucose, lactose, fructose, sorbital or mannitol and (ii) said pharmaceutically compatible water-soluble substance that liquefies under a water vapor tension of about 98 percent relative humidity is selected from sodium chloride, urea, malic acid and citric acid.

14. The transdermal therapeutic system as claimed in claim 12, wherein said active ingredient particles have a particle size that is less than 20% below the inclusion body particle size.

15. A method of protecting active ingredient micro- or nanoparticles within a transdermal therapeutic system from Ostwald ripening comprising forming inclusion bodies from water-soluble or water-swellable polymer containing active ingredient micro- or nanoparticles, drying the inclusion bodies and incorporating the dried inclusion bodies into a water insoluble outer phase.

16. The method as claimed in claim 15, wherein said micro- or nanoparticles have a diameter below 1 micron.

17. The method as claimed in claim 15, wherein the active ingredient saturation flux, calculated for a commercially relevant system area of 30 cm$^2$, is 50% or less of the therapeutically necessary dose.

18. The method as claimed in claim 15, wherein the transdermal therapeutic system is a transdermal patch.

* * * * *